(12) United States Patent
Karlinsey

(10) Patent No.: US 9,403,040 B1
(45) Date of Patent: Aug. 2, 2016

(54) CALCIUM-FREE COMPOSITION FOR DENTAL MINERALIZATION

(75) Inventor: Robert L. Karlinsey, Indianapolis, IN (US)

(73) Assignee: KARLINSEY ENTERPRISES, Indianapolis, IN (US)

( * ) Notice: Subject to any disclaimer, the term of this patent is extended or adjusted under 35 U.S.C. 154(b) by 0 days.

(21) Appl. No.: 13/555,673

(22) Filed: Jul. 23, 2012

Related U.S. Application Data

(60) Provisional application No. 61/639,334, filed on Apr. 27, 2012.

(51) Int. Cl.
| | |
|---|---|
| *A61Q 11/00* | (2006.01) |
| *A61K 8/21* | (2006.01) |
| *A61K 8/24* | (2006.01) |
| *A61K 8/19* | (2006.01) |
| *A61K 6/00* | (2006.01) |
| *A61K 8/02* | (2006.01) |

(52) U.S. Cl.
CPC .............. *A61Q 11/00* (2013.01); *A61K 6/007* (2013.01); *A61K 6/0082* (2013.01); *A61K 8/0216* (2013.01); *A61K 8/19* (2013.01); *A61K 8/24* (2013.01)

(58) Field of Classification Search
USPC ................................................ 424/49, 52, 57
See application file for complete search history.

(56) References Cited

U.S. PATENT DOCUMENTS

| | | | | |
|---|---|---|---|---|
| 4,353,892 | A * | 10/1982 | Caslavsky | A61Q 11/00 424/48 |
| 7,198,779 | B2 * | 4/2007 | Rifa Pinol et al. | 424/49 |
| 2003/0003219 | A1 | 1/2003 | Day et al. | |
| 2007/0275119 | A1 | 11/2007 | Lakkis | |

FOREIGN PATENT DOCUMENTS

EP      0 137 436    *   4/1985

* cited by examiner

*Primary Examiner* — Lezah Roberts
(74) *Attorney, Agent, or Firm* — C. John Brannon; Brannon Sowers & Cracraft PC

(57) ABSTRACT

A method for the restoration of dentition, including dissolving a phosphate salt in water to define a calcium-free aqueous phosphate solution and applying the aqueous phosphate solution to dentition. The calcium-free aqueous phosphate solution has a phosphate concentration of between about 10 ppm and about 10000 ppm.

10 Claims, No Drawings

CALCIUM-FREE COMPOSITION FOR DENTAL MINERALIZATION

CROSS-REFERENCE TO RELATED APPLICATIONS

This utility patent application claims priority to provisional patent application Ser. No. 61/639,334, filed on Apr. 27, 2012.

TECHNICAL FIELD

This novel technology relates generally to chemistry and, more specifically, to a chemical composition for remineralizing dentition.

BACKGROUND

Tooth strengthening, or remineralization, naturally occurs through the deposition of salivary minerals such as calcium and phosphate. It has been realized that the addition of fluoride can expedite the remineralization process. Additionally, the chemical interaction of fluoride with tooth mineral yields a benefit enjoyed by fluoridated enamel, insofar that it is less soluble than non-fluoridated enamel. Therefore, fluoridation continues to be an effective dental agent against mineral loss. Nevertheless, statistics continue to reveal that tooth decay remains problematic. Thus, improving remineralization remains a challenging problem and opportunity.

It has been realized that the addition of metal ions and/or minerals to fluoride can improve remineralization benefits. For example, a functionalized tricalcium phosphate system with or without fluoride can contribute to improved dentition remineralization. Likewise, the use of a milk-derived calcium phosphate system may be useful for mineralization purposes. Still another example is the use of nano-sized hydroxyapatite in combination with fluoride. Yet another example is the provision of amorphous calcium phosphate to dentition, with or without fluoride. Separately, fluoride combined with metal ions such as iron, titanium or tin may also provide improved dental benefits relative to fluoride alone.

While the above-mentioned approaches may provide benefits, nevertheless tooth decay remains problematic. Often, combination systems may not provide sufficient mineral integration with the tooth. One reason is due to the undesirable interactions between calcium and fluoride that can occur in an aqueous dental preparation. Often, dental preparations are designed to be compartmentalized or prepared in the absence of water to reduce the unwanted calcium-fluoride interactions during shelf-life. When the minerals are ultimately released in the oral cavity, in addition to reacting with the tooth, the minerals also react with each other, thus reducing bioavailability and uptake into the tooth structure. This limited remineralization is one drawback from some of the calcium and phosphate-based approaches. Additionally, the limited remineralization that does occur may break down, rendering the tooth susceptible to repeated acid-attack. Separately, the use of metallic species may not provide acceptable aesthetic or sensory qualities, and may contribute elevated risk factors for patient populations prescribed with certain medications.

Since basic tooth structure is apatite-like and is therefore comprised of calcium and phosphate elements, and since saliva contains both calcium and phosphate, it is commonplace and expected to include calcium with phosphate for the remineralization of dental tissues. During demineralization both calcium and phosphate are lost from the tooth. Since the loss of mineral is not slanted towards calcium or phosphate, therapeutic approaches involve supplying new sources of calcium and phosphate (with or without fluoride) to the weakened tooth structure.

Thus, there remains a need for a dental remineralization strategy that does not suffer the shortcomings of premature metal-fluoride interactions during shelf-life. The present novel technology addresses this. In this disclosure, we describe a non-obvious, unique approach of strengthening weakened teeth. In doing so, the approach avoids the weaknesses of many of calcium-added dental preparations, while improving on the remineralization of the teeth.

SUMMARY

The present novel technology corresponds to the general improvement in remineralization of weakened teeth. One important feature of this invention is the novel incorporation of a non-calcium agent. Another is the use of water-soluble phosphate-containing salts to provide rehardening of demineralized enamel at the teeth surface and subsurface. The combination of water-soluble phosphate salts and fluoride produces significant rehardening of weakened enamel relative to the application of a phosphate salt or fluoride alone. This novel technology may be implemented into dental vehicles, with or without fluoride, including toothpastes, rinses, varnishes, gums, mints, gels, and the like.

DETAILED DESCRIPTION

Tooth mineral is largely constructed of apatite, typically having a calcium to phosphate ratio of about 5:3. As practiced and taught throughout dentistry, the combination of calcium and phosphate are both critical to tooth structure, and it is considered axiomatic to strive for regularly restoring calcium and phosphate lost due to acid attacks and/or physical attrition. Physiologically, these minerals are naturally supplied by the saliva. However, supplements or additional mineralizing dental preparations containing calcium and phosphate may also provide increased concentrations of these minerals to the dentition.

Discussions surrounding mineralization, remineralization, and the like customarily include both calcium and phosphate and not one mineral without the other; that is, calcium and phosphate are typically discussed in conjunction. If calcium and phosphate are discussed separately, calcium is generally considered the most important species, since fluoride and phosphate and carbonate and hydroxide ions readily coordinate with calcium to produce mineralization. It is conventional wisdom that the composition of mineral lost due in typical carious lesions in human enamel is largely comprised between about 30% and about 40% calcium content. In stark contrast, between 13 and 18.5% phosphorous content is lost, which is about half of the content of calcium lost. It has been demonstrated that a 5:3 calcium to phosphate ratio remineralized softened enamel better relative to a calcium to phosphate ratio of 1:1. Therefore, the obvious and customary approaches in restoring lost mineral have focused on calcium-containing compositions.

The novel technology does not include calcium in the remineralization of weakened teeth. The novel technology pertains to non-calcium agents that may be combined with fluoride for improved remineralization of teeth.

Currently, phosphate may be added in the form of phosphoric acid and sodium phosphate monobasic when coupled with fluoride for the remineralization of enamel. Examples of dental preparations containing fluoride and phosphoric acid include, for instance, Colgate® Phos-Flur® fluoride gel (pH about 5.1) or acidulated fluoride mouth rinses, which are both low pH formulations comprising phosphoric acids (Jacques M. Dublin) As outlined in the Food & Drug Administration anticaries monograph 21CFR355.10 for anticaries active ingredients the pH of acidulated phosphate fluorides can range between 3.0 and 4.5. These formulations typically contain about 0.1M phosphate (about 9,600 ppm phosphate), and are typically comprised of phosphoric acid and sodium phosphate monobasic. These low pH systems typically lead to enhanced fluoride uptake due to simultaneous dissolution of apatite (which dissolves at pH less than 5.5) and corresponding fluoride uptake. Based on the fluoride monograph and commercially marketed acidulated phosphate fluoride formulations, the typical concentration ratios of fluoride to phosphate range from at least 1:5 up to about 1:50. Or, put in other words, the phosphate to fluoride ratios typically range from about 50:1 to about 5:1.

The present novel technology relates to the addition of water-soluble phosphate salts in the absence of calcium from about 10 ppm phosphate to about 5,000 ppm phosphate. In contrast to existing wisdom and practice, the instant invention is especially useful when the fluoride content is much greater than phosphate content (such as present in a ratio of about 10:1 more). Also, the system can function independently of the presence of phosphoric acid. Furthermore, the phosphate salt may be combined with fluoride in the above given amounts (ratios and concentrations) for mineralization of enamel. One benefit of the instant system is that thorough rinsing with water is not required after its application to prevent unwanted tooth mineral dissolution. This contrasts markedly with acidulated phosphate fluoride dental preparations, which must be rinsed away such that the dentition is not continuously damaged by standing acid. Demonstrated benefits of the novel system are detailed in the following examples.

Example 1

A pH cycling regimen was performed to demonstrate the effects of fluoride supplemented with water-soluble potassium dihydrogen phosphate. Six treatment groups were evaluated in this model:

1. distilled water;
2. 0.22% NaF (1,000 ppm F);
3. 0.22% NaF (1,000 ppm F)+0.01% $KH_2PO_4$ (100 ppm $PO_4$) (1:10 P-to-F);
4. 0.22% NaF (1,000 ppm F)+0.07% $KH_2PO_4$ (500 ppm $PO_4$) (1:2 P-to-F);
5. 0.22% NaF (1,000 ppm F)+0.14% $KH_2PO_4$ (1,000 ppm $PO_4$) (1:1 P-to-F); and,
6. 0.22% NaF (1,000 ppm F)+0.71% $KH_2PO_4$ (5,000 ppm $PO_4$) (5:1 P-to-F).

Three millimeter diameter bovine enamel was initially demineralized using a polyacrylic-lactic acid solution, saturated 50% with hydroxyapatite and pH adjusted to 5.0. Baseline surface microhardness measurements were made (Vickers, 200 gF, 15 sec dwell time, four measurements per specimen). Each treatment group had five enamel specimens that were cycled through the model listed below in Table 1 for 10 days.

TABLE 1

Outline of pH cycling model.
Interim surface microhardness measurements were made after five days of cycling, and then again after 10 days of cycling. Additionally, subsurface microhardness measurements were also made. The results from these measurements are listed below in Tables 2 and 3, respectively.

| Event | Duration |
|---|---|
| Treatment #1 | 1 minute |
| Saliva, pH = 7.0 | 1 hour |
| Treatment #2 | 1 minute |
| Saliva, pH = 7.0 | 1 hour |
| Acid Challenge, pH = 5.0 | 4 hours |
| Saliva, pH = 7.0 | 1 hour |
| Treatment #3 | 1 minute |
| Saliva, pH = 7.0 | 1 hour |
| Treatment #4 | 1 minute |
| Saliva, pH = 7.0 | Overnight |

TABLE 2

Mean (standard error of the mean) five- and ten-day post surface microhardness recoveries (% $SMHR^5$ and $SMHR^{10}$, respectively) results obtained by Vickers microhardness indents (N = 5).

| Groups | % $SMHR^5$ | % $SMHR^{10}$ |
|---|---|---|
| 0.0% F (control) | −0.6 (0.4) | 0.3 (0.7) |
| 0.22% NaF | 19.4 (4.3) | 21.5 (3.3) |
| 0.22% NaF + 0.01% $KH_2PO_4$ | 34.4 (4.6) | 50.6 (3.2) |
| 0.22% NaF + 0.07% $KH_2PO_4$ | 26.1 (6.9) | 52.7 (2.4) |
| 0.22% NaF + 0.14% $KH_2PO_4$ | 43.2 (4.6) | 55.2 (3.8) |
| 0.22% NaF + 0.71% $KH_2PO_4$ | 35.5 (3.8) | 47.5 (3.0) |

TABLE 3

Summary relative lesions size results (mean (standard error of the mean)) determined through cross-sectional microhardness (CSMH) measurements made after the 10-day cycling regimen (N = 5 × three measurement lanes).

| Groups | Relative Lesion Size ($\sqrt{KHN} \cdot \mu m$) |
|---|---|
| 0.0% F (control) | 522.7 (54.1) |
| 0.22% NaF | 247.1 (38.8) |
| 0.22% NaF + 0.01% $KH_2PO_4$ | 52.2 (35.7) |
| 0.22% NaF + 0.07 % $KF_2PO_4$ | 118.0 (51.9) |
| 0.22% NaF + 0.14% $KH_2PO_4$ | 43.5 (34.9) |
| 0.22% NaF + 0.71% $KH_2PO_4$ | 121.5 (29.7) |

When combined with fluoride as shown above, supplementation with 100 ppm phosphate can produce significant surface and subsurface strengthening relative to fluoride alone. Further remineralization is achieved in this calcium-free system when the phosphate weight percent is about ten-fold less than the fluoride weight percent, or in equal concentration of fluoride and phosphate.

Detailed Example 2

A pH cycling regimen was performed in accord with Table 1 to demonstrate the enamel strengthening effects of fluoride supplemented with water-soluble potassium dihydrogen phosphate ($KH_2PO_4$). Six treatment groups were evaluated in this model:
1. 0.0% NaF (distilled water);
2. 0.044% NaF (200 ppm F);
3. 0.044% NaF (200 ppm F)+0.002% $KH_2PO_4$ (20 ppm $PO_4$) (1:10 P-to-F);
4. 0.044% NaF (200 ppm F)+0.01% $KH_2PO_4$ (100 ppm $PO_4$) (1:2 P-to-F);
5. 0.22% NaF (1,000 ppm F); and,
6. 0.22% NaF (1,000 ppm F)+0.002% $KH_2PO_4$ (20 ppm $PO_4$) (1:50 P-to-F).

Interim surface microhardness measurements were made after five days of cycling, and then again after 10 days of cycling. Additionally, subsurface microhardness measurements were also made. The results from these measurements are listed below in Tables 4 and 5, respectively.

TABLE 4

Mean (standard error of the mean) five- and ten-day post surface microhardness recoveries (% $SMHR^5$ and $SMHR^{10}$, respectively) results obtained by Vickers microhardness indents (N = 10).

| Treatment Groups | % $SMHR^5$ | % $SMHR^{10}$ |
| --- | --- | --- |
| 0.0% NaF | 0.6 (0.4) | 0.4 (0.4) |
| 0.044% NaF | 9.8 (1.0) | 27.4 (2.8) |
| 0.044% NaF + 0.002% $KH_2PO_4$ | 13.6 (1.3) | 34.4 (2.2) |
| 0.044% NaF + 0.01% $KH_2PO_4$ | 11.9 (1.5) | 31.2 (3.8) |
| 0.22% NaF | 30.3 (2.6) | 41.1 (3.0) |
| 0.22% NaF + 0.002% $KH_2PO_4$ | 36.3 (1.9) | 52.5 (2.2) |

TABLE 5

Summary relative lesions size results (mean (standard error of the mean)) determined through cross-sectional microhardness (CSMH) measurements made after the 10-day cycling regimen (N = 10 × three measurement lanes).

| Treatment Groups | Relative Lesion Size ($\sqrt{KHN} \cdot \mu m$) |
| --- | --- |
| 0.0% NaF | 517.5 (22.7) |
| 0.044% NaF | 248.0 (33.6) |
| 0.044% NaF + 0.002% $KH_2PO_4$ | 345.6 (30.4) |
| 0.044% NaF + 0.01% $KH_2PO_4$ | 232.8 (24.2) |
| 0.22% NaF | 185.9 (19.1) |
| 0.22% NaF + 0.002% $KH_2PO_4$ | 148.1 (26.2) |

When combined with fluoride as shown in Example 2 above, supplementation with about 0.002% (i.e. 20 ppm) phosphate to 200 or 1,000 ppm fluoride can produce greater surface and subsubsurface strengthening relative to fluoride alone. Further remineralization can be achieved in this calcium-free system when the phosphate weight percent is at 50-fold less than the fluoride weight percent.

Detailed Example 3

A pH cycling regimen was performed to demonstrate the effects water-soluble potassium dihydrogen phosphate ($KH_2PO_4$) in the absence of fluoride. Three treatment groups were evaluated in this model:
1. 0.0% $KH_2PO_4$ (distilled water);
2. 0.14% $KH_2PO_4$ (1,000 ppm $PO_4$); and,
3. 0.71% $KH_2PO_4$ (5,000 ppm $PO_4$).

Three millimeter diameter bovine enamel was initially demineralized using a polyacrylic-lactic acid solution, saturated 50% with hydroxyapatite and pH adjusted to 5.0. Baseline surface microhardness measurements were made (Vickers, 200 gF, 15 sec dwell time, four measurements per specimen). Each treatment group had five enamel specimens that were cycled through the model listed below in Table 6 for 10 days.

TABLE 6

Outline of pH cycling.

| Event | Duration |
| --- | --- |
| Simulated Saliva, pH = 7.0 | 1 hour |
| Acid Challenge #1, pH = 5.0 | 30 minutes |
| Simulated Saliva, pH = 7.0 | 1 hour |
| Treatment #1 | 9 minutes |
| Simulated Saliva, pH = 7.0 | 1 hour |
| Acid Challenge #2, pH = 5.0 | 30 minutes |
| Simulated Saliva, pH = 7.0 | 1 hour |
| Treatment #2 | 9 minutes |
| Simulated Saliva*, pH = 7.0 | 1 hour |
| Acid Challenge #3, pH = 5.0 | 30 minutes |
| Simulated Saliva, pH = 7.0 | 1 hour |
| Treatment #3 | 9 minutes |
| Simulated Saliva, pH = 7.0 | Overnight |

After five and ten days of cycling, surface and subsurface microhardness measurements were made. The results from these measurements are listed below in Tables 7 and 8, respectively.

TABLE 7

Mean (standard error of the mean) five- and ten-day post surface microhardness recoveries (% $SMHR^5$ and $SMHR^{10}$, respectively) results obtained by Vickers microhardness indents (N = 5).

| Treatment Groups | % $SMHR^5$ | % $SMHR^{10}$ |
| --- | --- | --- |
| 0.0% $KH_2PO_4$ | 4.6 (0.8) | 7.8 (0.2) |
| 0.14% $KH_2PO_4$ | 6.4 (1.3) | 12.0 (3.5) |
| 0.71% $KH_2PO_4$ | 5.6 (1.6) | 6.2 (2.0) |

TABLE 8

Summary relative lesions size results (mean (standard error of the mean)) determined through cross-sectional microhardness (CSMH) measurements made after the 10-day cycling regimen (N = 5 × three measurement lanes).

| Treatment Groups | Relative Lesion Size ($\sqrt{KHN} \cdot \mu m$) |
|---|---|
| 0.0% $KH_2PO_4$ | 327.6 (30.5) |
| 0.14% $KH_2PO_4$ | 205.7 (35.9) |
| 0.71% $KH_2PO_4$ | 293.9 (59.6) |

When combined with fluoride as shown in Example 3 above, supplementation with about 1,000 ppm phosphate in the absence of fluoride can produce greater surface and sub-subsurface strengthening relative to fluoride alone.

Detailed Example 4

A pH cycling regimen was performed to demonstrate the effects water-soluble potassium dihydrogen phosphate ($KH_2PO_4$) in the absence of fluoride. Two treatment groups were evaluated in this model:
1. 0.0% $KH_2PO_4$ (distilled water); and,
2. 0.07% $KH_2PO_4$ (500 ppm $PO_4$).
Three millimeter diameter bovine enamel was initially demineralized using a polyacrylic-lactic acid solution, saturated 50% with hydroxyapatite and pH adjusted to 5.0. Baseline surface microhardness measurements were made (Vickers, 200 gF, 15 sec dwell time, four measurements per specimen). Each treatment group had five enamel specimens that were cycled through the model listed in Table 6 for 10 days.

After five and ten days of cycling, surface and subsurface microhardness measurements were made. The results from these measurements are listed below in Tables 9 and 10, respectively.

TABLE 9

Mean (standard error of the mean) five- and ten-day post surface microhardness recoveries (% $SMHR^5$ and $SMHR^{10}$, respectively) results obtained by Vickers microhardness indents (N = 5).

| Treatment Groups | % $SMHR^5$ | % $SMHR^{10}$ |
|---|---|---|
| 0.0% $KH_2PO_4$ | 6.5 (1.7) | 11.7 (2.9) |
| 0.07% $KH_2PO_4$ | 15.1 (2.0) | 22.1 (1.8) |

TABLE 10

Summary relative lesions size results (mean (standard error of the mean)) determined through cross-sectional microhardness (CSMH) measurements made after the 10-day cycling regimen (N = 5 × three measurement lanes).

| Treatment Groups | Relative Lesion Size ($\sqrt{KHN} \cdot \mu m$) |
|---|---|
| 0.0% $KH_2PO_4$ | 399.1 (22.6) |
| 0.07% $KH_2PO_4$ | 300.9 (36.1) |

When combined with fluoride as shown in Example 4 above, supplementation with about 500 ppm phosphate can produce greater surface and subsubsurface strengthening relative to fluoride alone.

Phosphate, without fluoride, is typically present in aqueous solution in concentrations of between about 10 ppm and about 10,000 ppm, more typically between about 100 ppm and about 5000 ppm, and still more typically between about 200 ppm and about 1000 ppm. With fluoride present, phosphate is typically present in concentrations of between about 50 ppm and about 10,000 ppm, more typically between about 500 ppm and about 5000 ppm, and still more typically between about 500 ppm and about 2500 ppm. The fluoride-to-phosphate ratios are typically between about 1:5 and about 20:1, more typically between about 1:1 and about 10:1.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

I claim:

1. A calcium-free dental mineralizing combination, comprising:
    a calcium-free comestible portion;
    a calcium-free phosphate-containing portion mixed with the comestible portion; and
    a calcium-free fluoride-containing portion mixed with the comestible portion;
    wherein the concentration of phosphate is between about 10 ppm and about 50 ppm;
    wherein the concentration of fluoride is between about 200 ppm and about 500 ppm;
    wherein the calcium-free combination has a phosphate to fluoride ratio between 1:10 and 1:50.

2. The calcium-free combination of claim 1, wherein the calcium-free combination is selected from the group including gels, pastes, and varnishes.

3. The calcium-free combination of claim 1, wherein the calcium-free combination has a pH sufficiently high to not dissolve apatite.

4. The calcium-free combination of claim 3, wherein the calcium-free combination has a pH of about 5.5.

5. The calcium-free combination of claim 1, wherein the calcium-free fluoride-containing portion comprises a single salt of fluoride.

6. A calcium-free dental remineralizing composition, comprising:
    a calcium-free carrier portion;
    a calcium-free phosphate-containing portion mixed with the carrier portion; and
    a calcium-free fluoride-containing portion mixed with the carrier portion;
    wherein the calcium-free composition has a phosphate concentration of between about 10 ppm and about 50 ppm;
    wherein the calcium-free composition has a pH sufficiently high to not dissolve apatite;
    wherein the calcium-free composition has a phosphate to fluoride ratio of between about 1:10 and about 1:50.

7. The calcium-free composition of claim 6, wherein the calcium-free composition has a fluoride concentration of about 200 ppm.

8. The calcium-free composition of claim 6, wherein the calcium-free composition is selected from the group including gels, pastes, and varnishes.

9. The calcium-free composition of claim 5, wherein the calcium-free composition has a pH greater than 5.5.

10. The calcium-free composition of claim 6, wherein the calcium-free fluoride-containing portion comprises a single salt of fluoride.

\* \* \* \* \*